United States Patent
Kirn

[11] Patent Number: 5,921,980
[45] Date of Patent: Jul. 13, 1999

[54] LASER SKIN GRAFT HARVESTING APPARATUS AND RELATED METHOD

[75] Inventor: David S. Kirn, Lexington, Ky.

[73] Assignee: University of Kentucky Research Foundation, Lexington, Ky.

[21] Appl. No.: 08/984,651

[22] Filed: Dec. 3, 1997

[51] Int. Cl.[6] ................................................ A61B 17/32
[52] U.S. Cl. .................... 606/2; 66/9; 66/13; 128/898
[58] Field of Search .................... 606/2, 3, 8, 9, 606/13, 16–18, 167, 170

[56] References Cited

U.S. PATENT DOCUMENTS

| | | |
|---|---|---|
| 2,428,018 | 9/1947 | Eldam . |
| 2,540,462 | 2/1951 | Smith . |
| 2,590,299 | 3/1952 | Douglas . |
| 3,640,279 | 2/1972 | Brown et al. . |
| 3,782,387 | 1/1974 | Falabella . |
| 4,690,139 | 9/1987 | Rosenberg . |
| 4,838,284 | 6/1989 | Shelanski . |
| 4,849,859 | 7/1989 | Nagasawa . |
| 5,219,352 | 6/1993 | Atkinson . |
| 5,236,323 | 8/1993 | Long et al. . |
| 5,254,115 | 10/1993 | Bhatta et al. .............................. 606/16 |
| 5,300,065 | 4/1994 | Anderson ................................... 606/13 |
| 5,423,803 | 6/1995 | Tankovich et al. . |
| 5,571,098 | 11/1996 | Domankevitz et al. . |

*Primary Examiner*—Lee Cohen
*Assistant Examiner*—Roy Gibson
*Attorney, Agent, or Firm*—King and Schickli

[57] ABSTRACT

A laser dermatome is disclosed for harvesting and meshing grafts of skin. A roller driven by a motor lifts the leading edge of a portion of skin for cutting by a beam of light generated by a laser. Adhesive tape attached to the roller aids in lifting the portion of skin and is further utilized to secure the severed portion of skin to the roller. A stage mounted atop an axle supports the laser or a beam director. The movement of the stage is controlled by second and third motors which drive the stage along or rotate it about the axle providing directional control of the laser. A controller controls the motors and synchronizes the movements of the roller and stage dependent upon inputs from the operator and sensors during operation. In the related method, a portion of skin to be harvested is lifted by the roller and cut by the laser beam. The controller signals the motor to drive the roller, thereby lifting the severed portion of skin and exposing the next portion for further cutting by the laser. These steps are repeated until the desired size graft is obtained. The laser is secondarily utilized to perform the additional step of meshing the graft in order to allow expansion of the graft to cover a larger area.

15 Claims, 6 Drawing Sheets

LASER SKIN GRAFT HARVESTING APPARATUS AND RELATED METHOD

TECHNICAL FIELD

The present invention relates to the field of dermatomes for surgically harvesting grafts of skin for transplant, and more particularly to a laser dermatome apparatus for harvesting and meshing grafts of skin utilizing a laser beam of light as the cutting mechanism.

BACKGROUND OF THE INVENTION

Laser surgery in general has become an important advancement in the medical profession over the last several years. Lasers are used in numerous surgical procedures. In the field of plastic surgery alone various types of lasers are prominently utilized in performing a variety of procedures. For example, yellow pulsed-dye lasers are used in the removal or lightening of port-wine stain birthmarks, and the Q-switch ruby, Q-switch YAG, and the alexandrite lasers are used to remove decorative and traumatic tattoos, pigmented lesions, and brown patches and spots. Carbon dioxide lasers are used successfully in a surgical procedure to remove warts and skin growths, and argon lasers are used to treat abnormalities that have a proliferation of blood vessels, such as blood blisters, spider blood vessels on the face, strawberry birthmarks, hemangiomas and bulky vascular tumors. Despite this wide variety of laser types and procedures performed, a laser has never been used to harvest a graft of skin.

A skin graft is a patch of healthy skin that is taken from one area of the body, called the donor site, and used to cover another area where skin is missing or damaged. There are three basic types of skin grafts including a split-thickness, a full-thickness, and a composite skin graft. The split-thickness graft is commonly used to treat burn wounds and uses only the layers closest to the surface. The full-thickness graft is used for areas where thicker tissue is desired and post operative wound contracture must be minimized such as jointed areas where maximum elasticity and movement are required. Full thickness grafts include all of the layers of the skin. A composite graft is used for complex reconstructive purposes such as with skin cancer on the nose and includes removing all of the skin layers, fat and sometimes the underlying cartilage from the donor site.

Split thickness skin grafting is one of the most commonly performed surgical procedures. This process involves shaving a sheet of skin including the entire epidermal layer as well as a portion of the dermis. At present in so far as can be determined, only mechanical dermatomes similar to those shown in U.S. Pat. Nos. 4,690,139 to Rosenberg and D322, 672 to Brown, for example, have been successfully utilized in harvesting split thickness skin grafts. These mechanical-type dermatomes typically include an oscillating blade driven by a pneumatic or electrical means for cutting the skin.

One critical shortcoming inherent in the use of these prior art devices is the relatively large amount of blood loss resulting from the cutting of the highly vascularized top layers of skin. In addition, post operative weeping from the lymphatic channels in the skin retards the recovery time and further contributes to the prolonged discomfort of the patient at the donor site. These shortcomings are of increased importance in the treatment of burn victims who require extensive grafting procedures.

An additional shortcoming inherent in the use of mechanical dermatomes is the general distortion of and damage to the graft tissue caused by the force of the cutting blade moving through the skin. This distortion often results in both nonuniform sizes and thicknesses of grafts and is greatly increased by the inevitable dulling of the cutting blade. In a worst case scenario, a dull cutting blade can result in the creation of a wound for the patient without the successful harvest of a graft.

Further, all existing mechanical dermatomes harvest generally rectangular grafts only. Since few wounds are rectangular, the surgeon must trim the graft to fit the wound. This creates additional steps for the surgeon, wastes donor skin and contributes to patient morbidity without benefit.

In the majority of skin graft transplant cases, harvested split thickness skin grafts are subsequently meshed to allow the graft to be expanded to cover a larger area. This process minimizes the size and morbidity of the donor site. However, this process again requires additional steps in the surgical procedure and an additional meshing apparatus.

It is contemplated that these shortcomings in the surgical procedure of harvesting and meshing grafts of skin can be alleviated by utilizing a beam of light generated by a laser as the cutting mechanism. Specifically what is needed is an apparatus capable of generating and controlling a laser beam for efficiently cutting, and, if necessary, meshing segments of skin being harvested from a donor body for successfully performing a grafting operation for a recipient.

SUMMARY OF THE INVENTION

Accordingly, it is a primary object of the present invention to provide a skin graft harvesting apparatus and related method for overcoming the limitations of the prior art.

It is another object of the present invention to provide an apparatus and related method for harvesting segments of skin from a body utilizing a laser, thus limiting blood loss and weeping from the donor site, and deformation of the skin caused by mechanical cutting forces.

Still another object of the present invention is to provide an apparatus and related method for harvesting a portion of skin utilizing precision control methods to reduce the reliance on surgical expertise, thereby improving the quality of grafts by providing a more uniform size and thickness.

Yet another object of the present invention is to provide an apparatus and related method for harvesting portions of skin of varying and/or specific sizes, shapes and thicknesses for use as a graft dependent upon individual recipient needs.

It is a related object of the present invention to provide an improved method/apparatus capable of harvesting and meshing a portion of skin for use as a graft in one operation using a laser to cut and mesh the portion of skin.

Additional objects, advantages, and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention as described herein, there is provided a laser dermatome apparatus for harvesting and meshing grafts of skin utilizing a beam of light generated by a laser as the cutting mechanism. In accordance with the method of the present invention, a skin lifting element is utilized to lift a portion of skin for cutting with the laser beam of light. The laser beam is directed toward the raised portion of skin, effectively cutting the skin. The cut portion of skin adheres to the skin lifting element allowing the next portion of skin to be cut by the laser beam. Portions of skin are progressively severed by the laser beam until a segment of skin of the desired dimensions of length, width and thickness is obtained.

In accordance with an important aspect of the present invention, the utilization of a laser beam to sever the skin prevents excessive blood loss and weeping from the donor site during surgery and the early postoperative period. Specifically, the laser beam cauterizes the small bleeding vessels in the dermis transected by the laser beam as it cuts the tissue, thereby significantly decreasing blood loss. In addition, the lymphatic channels are also cauterized, thus limiting postoperative weeping at the donor site.

The utilization of the laser beam to sever the segment of skin also reduces the need to harvest oversized grafts which must later be trimmed to the proper size or to remove damaged tissue prior to being transplanted. Advantageously, modern lasers, such as carbon dioxide lasers, transfer a large amount of energy in a relatively short amount of time. Accordingly, the pulse duration of the laser is maintained below the thermal relaxation time of the skin, thus allowing only the tissue on which the laser beam is incident to be vaporized while the surrounding skin cells are left undamaged.

The synchronization of the skin lifting element and the laser beam during the harvesting procedure are accomplished using a controller. In particular, the controller is utilized to synchronize the movements of drive motors in accordance with the operator's input and feedback from varying sensors. Advantageously the ability to synchronize and precisely control the movements of the lifting element and the laser beam greatly reduces the need to harvest oversized grafts, as well as, the present reliance on surgical expertise.

The method of harvesting a segment of skin from a body for grafting may include the additional step of meshing the segment of skin to allow the graft to be stretched to cover a larger area than the original donor site. This is accomplished by directing the laser beam of light to make generally parallel cuts typically perpendicular to the primary cuts, along each portion of skin at predetermined intervals.

Still other objects of the present invention will become apparent to those skilled in this art from the following description wherein there is shown and described the preferred embodiments of this invention, simply by way of illustration of some of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification, illustrates several aspects of the present invention, and together with the description serves to explain the principles of the invention. In the drawings:

FIG. 4 is a side elevational view showing the tandem movements of the support frames of the laser dermatome utilized to direct the laser beam of light to control the size, shape and thickness and the meshing of the graft.

Reference will now be made in detail to the present preferred embodiment of the invention, an example of which is illustrated in the accompanying drawing.

DETAILED DESCRIPTION OF THE INVENTION

Figure 1:
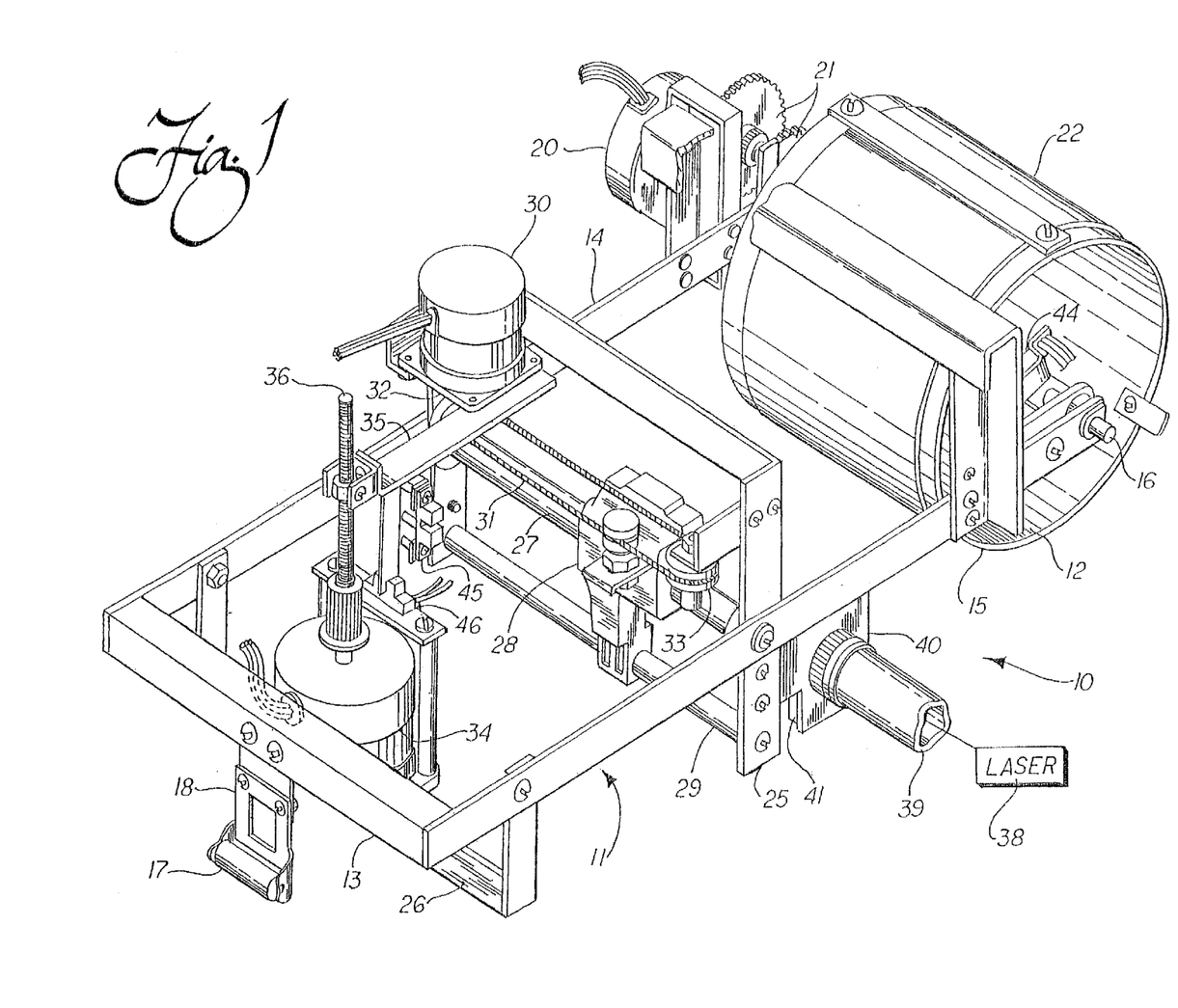
FIG. 1 is a perspective view of the support frame with skin lifting element, drive motors and beam director and shows the lateral movement of the stage which supports the beam director.
Figure 2:
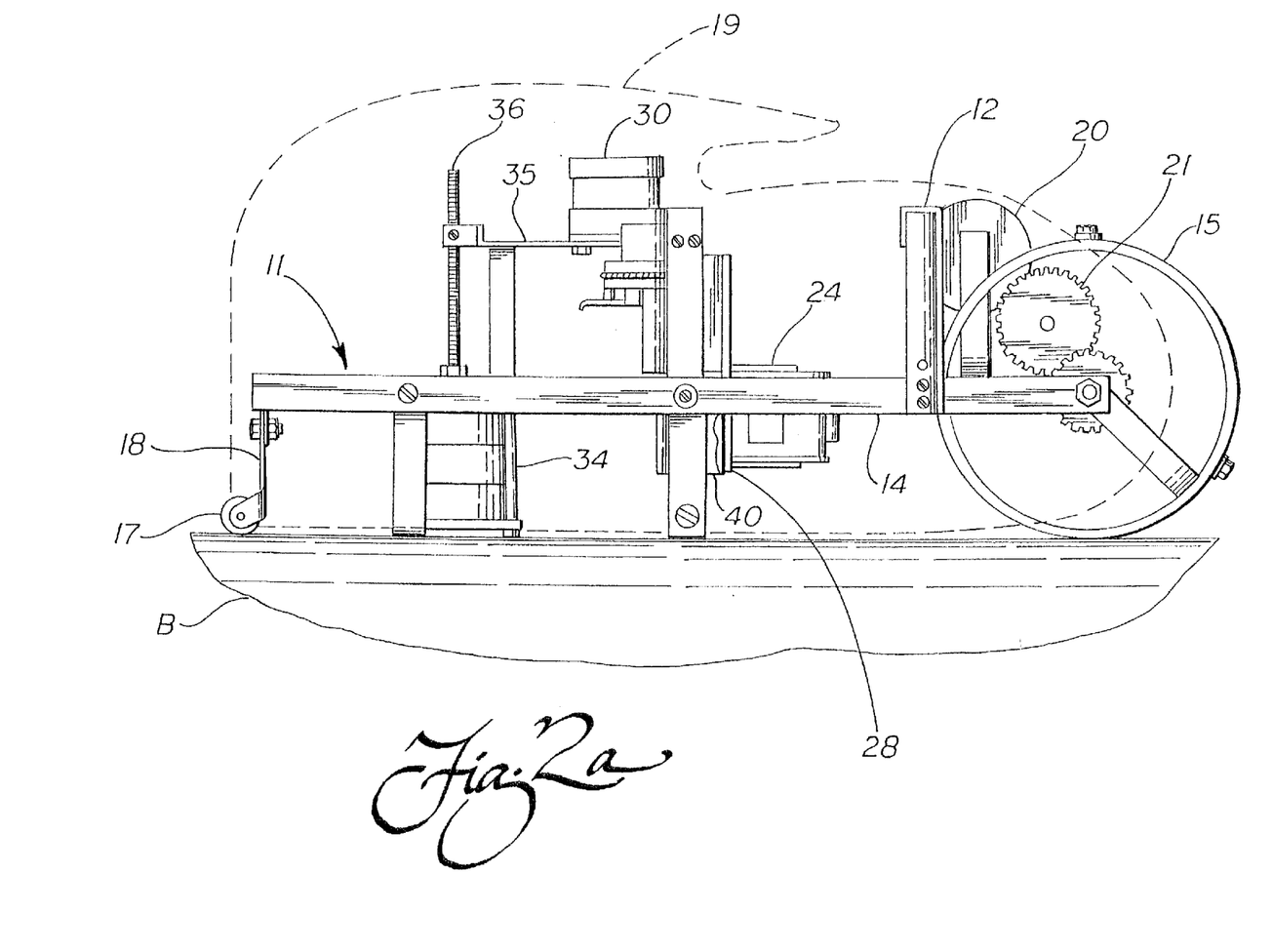
FIG. 2A is a side elevational view showing the laser dermatome at a first position resting on a body from which the segment of skin will be harvested.
FIG. 2B is a partial side elevation view showing the laser dermatome at a second position lifting a portion of skin for cutting by the laser.
FIG. 2C is a partial side elevational view showing the laser dermatome at a third position holding the severed portions of skin to the roller and lifting the next portion of skin for further cutting by the laser.
Figure 2B:
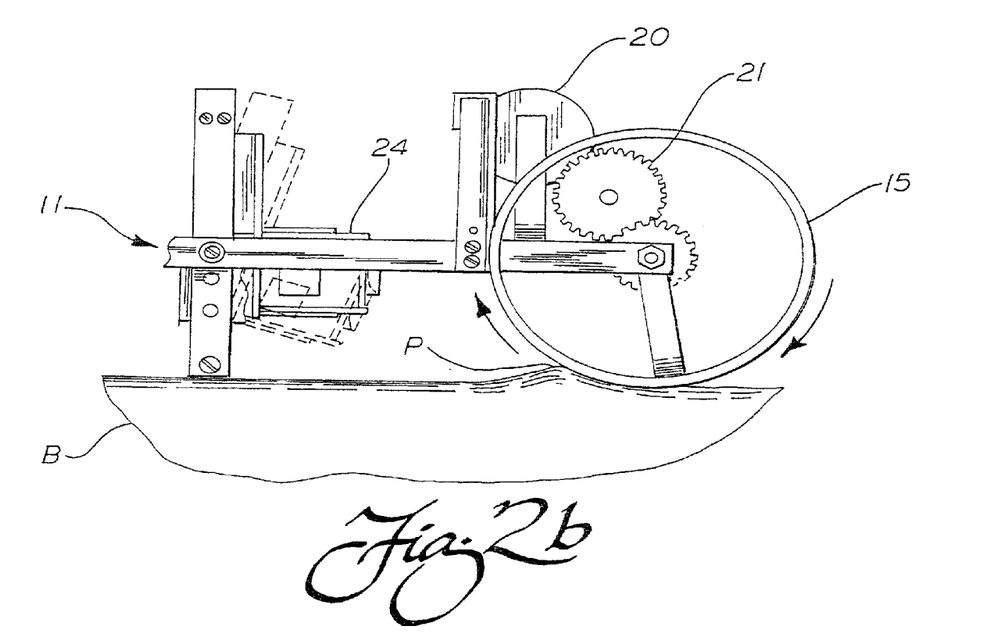
Figure 2C:
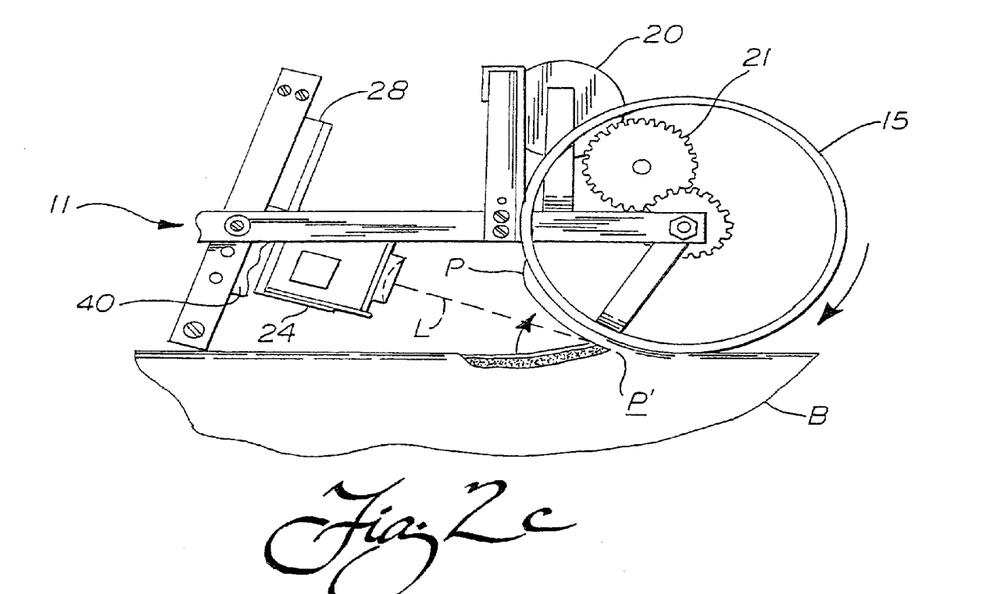

With reference to the perspective view of FIG. 1, there is shown a preferred embodiment of a laser dermatome 10 for use in harvesting and meshing segments of skin to be used as a graft. As best illustrated in FIGS. 2A–2C, the laser dermatome 10 is placed on a body B; a portion of skin to be harvested is lifted by the dermatome and cut utilizing a beam of light L generated by a laser. The resulting segment of skin forms a graft for later transplant. For purposes of illustration, it will be assumed that the portion of skin is located at the anterior thigh area of a human body; however, it is to be understood that the present invention may be utilized to harvest a graft of skin from any area of the human body, as well as, any area of the bodies of other species of animals.

In this preferred embodiment, a platform, generally designated by the reference numeral 11, includes a front cross rail 12, a rear cross rail 13, and a pair of side rails 14 extending beyond the frontcross rail. A roller 15 having an axle 16 is rotatably attached between the ends of the pair of side rails 14 such that the roller is free to rotate along its center axis. A wheel 17 is also rotatably attached to a support bar 18. As best shown in FIG. 2A, the support bar 18, wheel 17 and roller 15 act as support legs allowing the moving portions of the dermatome 10 to operate within a housing 19 (shown in phantom and only in FIG. 2A for clarity) and free from obstruction caused by contact with the donor body B. The housing 19, in the present preferred embodiment, is made of a sterilisable molded plastic. It should be appreciated that various other apparatus known in the art may also be utilized to support the dermatome 10 above the donor body B.

As further shown in FIG. 2A and sequentially in FIGS. 2B–2C, the roller 15 operates to lift a portion of skin P for cutting by a beam of light L generated by a laser. A first motor 20 mounted to the platform 11 is utilized to drive the roller 15 in a controlled manner. In this preferred embodiment, planetary gears 21 transfer the torque delivered by the shaft of the motor to the roller's axle 16, thereby causing the roller 15 to rotate. The first motor 20, in an alternate embodiment of the present preferred embodiment, may be positioned within the roller 15 to reduce the overall size of the dermatome.

Also in the preferred embodiment of the present invention, a removable adhesive tape 22 of a kind generally known in the art is secured around at least a portion of the outer periphery of the roller 15 using a suitable attachment means. The adhesive tape 22 adheres to the portion of skin P to be cut and, as the roller 15 is driven forward, operates to lift the portion of skin P for cutting by the laser beam L. As best shown in FIG. 2C, the severed portions of skin P are firmly held against the outer periphery of the roller 15, thus allowing the laser beam L to cut the next portion of skin P' until the desired size and shape segment of skin is severed from the body.

Figure 3:
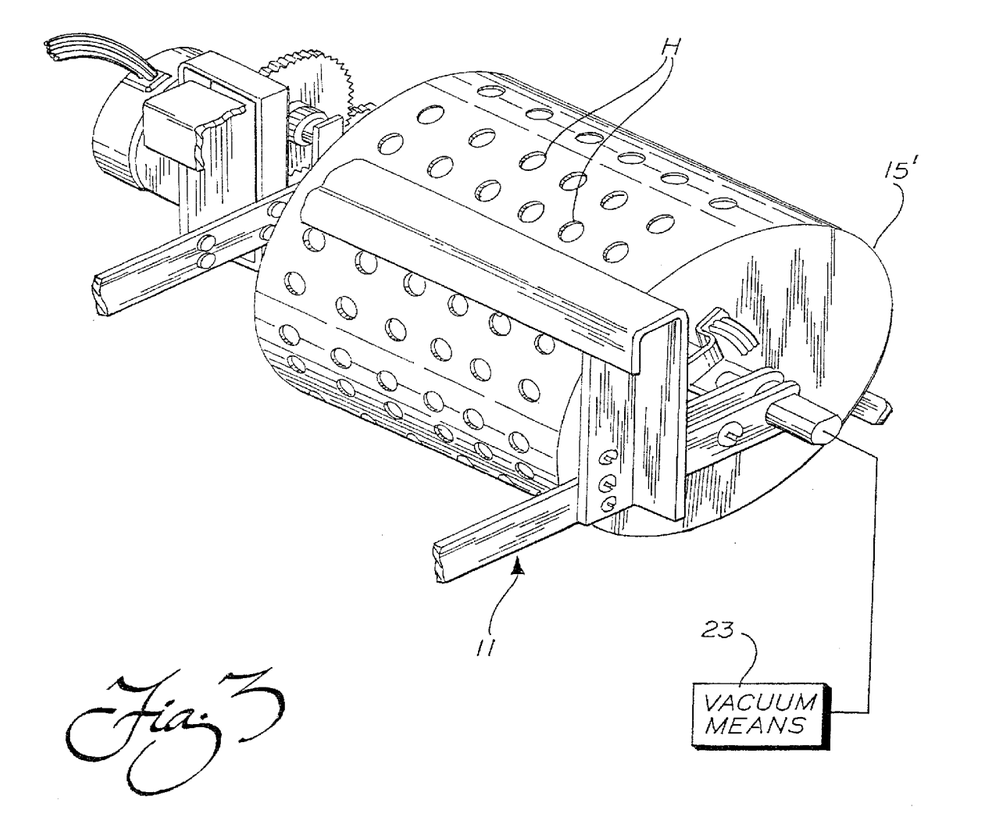
FIG. 3 is a partial perspective view of an alternate embodiment of the present preferred embodiment showing the support frame with a perforated skin lifting element attached to a vacuum means for lifting the portion of skin to be cut and holding the severed portions of skin.

In accordance with the broadest aspects of the present invention, any means may be used to lift the portion of skin P for cutting by the laser beam L. For example, as shown in FIG. 3, an alternate embodiment may include a vacuum means 23 attached to a roller 15' having perforations H along at least a portion of its periphery. The vacuum means 23 creates a vacuum which acts in a similar manner as the adhesive tape 22, lifting the portion of skin P for cutting by the laser beam L and securing the cut portions such that the next portion of skin P' may also be cut.

As best shown in FIG. 1, the moving portions of the dermatome 10 discussed briefly above include support frames 25 and 26 attached between the pair of side rails 14. More specifically, an inverted U-shaped support frame 25 is pivotally attached to the side rail pair 14 generally midway between the front and rear cross rails.

A first guide shaft 27 is also pivotally attached between the side rail pair 14 concentric with the pivot axis of the support frame 25. A stage 28 is provided for supporting a beam director 24 for directing the laser beam L toward the portion of skin P lifted by the roller 15. A second guide shaft 29 is attached between the open leg ends of the support frame 25. The second guide shaft 29 operates to assist the translational movement of the stage 28 about the axis of the first guide shaft 27, as discussed more fully below.

In this preferred embodiment, a second motor 30 is utilized to provide a pushing/pulling force sufficient to drive the stage 28 laterally, as shown by directional arrow A in FIG. 1, along the guide shafts 27, 29 from side-to-side. A cord 31 wrapped around the motor shaft 32 at one end and a pulley 33 at the other end transfers the motor shaft torque to the attached stage 28, thus controlling the width of the segment of skin to be harvested.

As shown in FIG. 4, a third motor 34 is mounted on support frame 26. A lever 35 is operatively connected to a shaft 36 of the third motor 34 at one end and extends toward and is connected to support frame 25 at the other end. The rotation of the motor shaft 36 operates to raise/lower the lever 35, thereby providing translational movement of the stage 28 and beam director 24 as shown by reference arrows C and D.

More specifically, support frame 26 is U-shaped and pivotally attached to the side rail pair 14 near the top end of each leg. This pivotal attachment allows support frames 25 and 26 to move in tandem and provides for translational control of the stage 28, beam director 24 and laser beam L, thereby determining the thickness of the graft.

Again in accordance with the broadest aspects of the present invention, various means may be utilized to control the lateral/translational movement of the stage 28/beam director 24. For instance, the motors/pulley system which make up the moving portions of the dermatome 10 described above may be replaced with a more fluid linear motion system. Any method of controlling the movement of the stage known in the art may be utilized such as ball screw drives, rack and pinion slides, various linear ball bearing systems and/or even linear/rotary translational positioning stages. In accordance with the broadest aspects of the present invention, each of these and other alternate embodiment control methods/apparatus clearly fall within the scope of the present invention as defined by the appended claims.

In the present preferred embodiment, a pulsed carbon dioxide laser 38 is utilized to generate the necessary laser beam of light L. Advantageously, carbon dioxide lasers transfer a large amount of energy in a relatively short amount of time. Accordingly, the pulse duration of the laser is maintained below the thermal relaxation time of the skin, thus allowing only the tissue on which the laser beam is incident to be vaporized while the surrounding skin cells are left undamaged.

As best shown in FIG. 1, in the present preferred embodiment, the laser 38 is mounted apart from the dermatome 10. The beam of light L generated by the laser 38 is directed to the dermatome 10 through an articulate arm 39. The articulate arm 39 mates with receiving plate 40 of the dermatome 10. In accordance with the broadest aspects of the present invention, various articulate arms may be used depending upon the selected laser. The receiving plate 40 is attached to support frame 25, thus causing the articulate arm to move translationally in tandem with the stage 28 and beam director 24. This allows the beam of light L to pass unobstructed through plate 40 and to be directed toward beam director 24 where it is reflected at a generally 90 degree angle toward the portion of skin P to be severed. Again, in accordance with the broadest aspects of the present invention, any type of beam director sufficient to direct the laser beam L may be used. The beam director 24, for example, may be an off-axis parabolic mirror or an appropriate lens/mirror assembly.

In an alternate embodiment of the present preferred invention, the laser 38 may be mounted to stage 28 and focused upon the portion of skin P to be severed.

Figure 5:
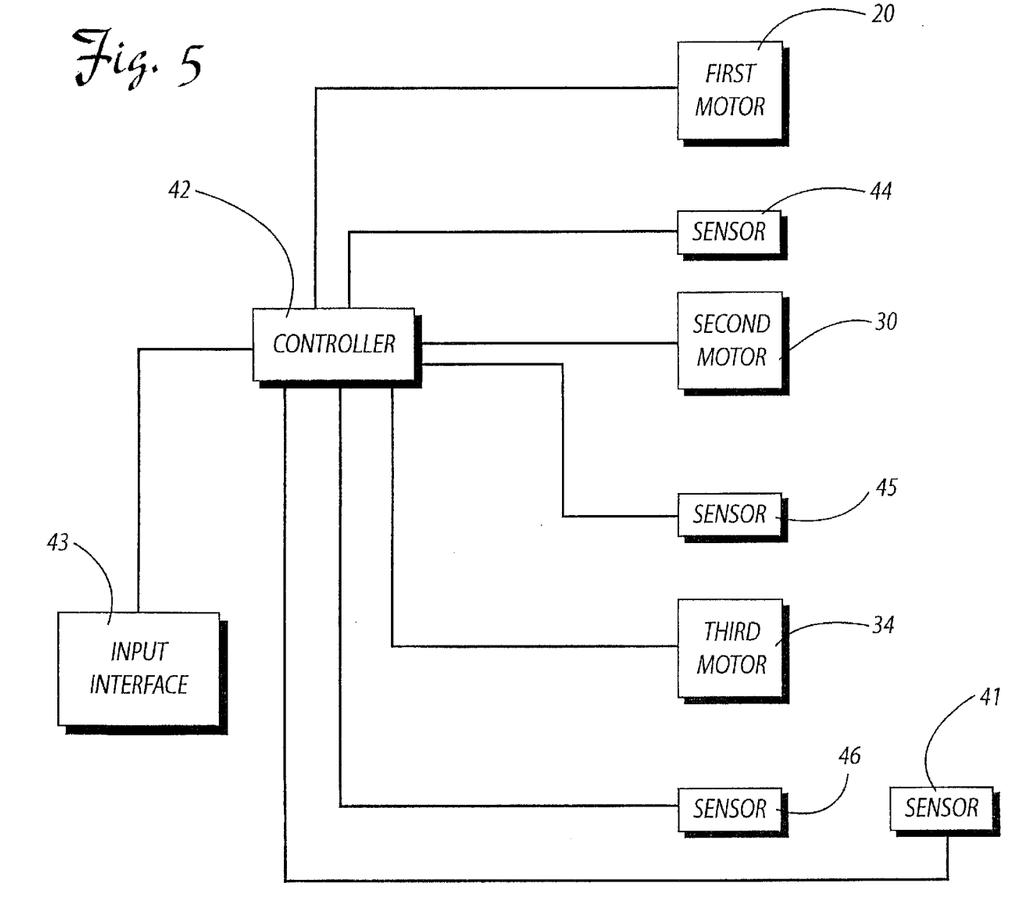
FIG. 5 is a schematic block diagram of the control system of the laser dermatomes.

As shown in FIG. 1 a sensor 41, such as a photoelectric sensor, mounted to the interior of the receiving plate 40, operates to detect the presence of the laser beam L. As best shown schematically in FIG. 5, upon detection of the laser beam L, the sensor 41 sends a signal to a controller 42. The controller 42 operates to control/coordinate the movements of each drive motor 20, 30 and 34 dependent upon the predetermined inputs of the surgeon. These inputs include the length, width, thickness and meshing ratio, if required, of the graft to be harvested, and can be entered utilizing any type of input interface 43, such as a keyboard, keypad or even remotely using infra red or radio transmitters/receivers. Sensors 41, 45 and 46 provide additional feedback signals to the controller 42 regarding the real time alignment of the roller 15 and stage 28.

In accordance with the method of harvesting a skin graft, a portion of skin is incrementally lifted by the rotation of the roller 15 and adhesive tape 22. This incremental lifting is controlled by the controller 42 and first motor 20. The width and thickness of the segment of skin, as noted above, is predetermined by the surgeon's inputs via the input interface 43 and is used by the controller 42 to activate motor 34 to position the stage 28 for the proper thickness. The laser 38 is then triggered to fire or pulse a beam of light L. This pulse is detected by sensor 41 and a corresponding signal is sent to the controller 42. The controller then signals the second motor 30 to move the stage 28 a distance equivalent to the diameter of the laser beam L. This cycle is repeated until the predetermined width portion of skin is severed. At this time, the controller 42 signals the first motor 20 to rotate the roller 15 a specified distance, thereby lifting the next portion of skin P'.

Meanwhile, the severed portions of skin adhere to the roller 15, thus securing the cut portion away from the path of the laser beam L. Upon completion of the incremental rotation of the roller 15, the stage 28 is again driven laterally by the second motor 30 and operates to cut along the predetermined width of the portion of skin P'. It should be appreciated that these steps are repeated until the predetermined length of graft is obtained.

Additionally, the laser beam L may be secondarily utilized to mesh the segment of skin to be used as a graft during the harvesting process. The third motor 34 which primarily controls the thickness of the graft operates to direct the laser beam L such that additional cuts in the lifted portion of skin are made. These secondary cuts are typically perpendicular to the primary cuts made by the laser beam L and accommodate any necessary expansion of the harvested graft. For example, these secondary cuts can be made in any ratio, such as 1.5:1, 2:1, or 3:1, depending upon the graft recipient's need. The controller 42 operates to control the ratio.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration o the principles of the invention and its practical application to thereby enable one of ordinary skill in the art to utilize the invention in various embodiments and with various modifications as is suited to the particular use contemplated. All such modifications and variations are within the scope of the invention as determined by the appended claims when interpreted in a accordance with the breadth to which they are fairly, legally and equitably entitled.

I claim:

1. An apparatus for harvesting a segment of skin from a body for later use as a graft, comprising:

a support frame;

a skin lifting element mounted to said support frame for lifting and removing a portion of cut skin;

a skin cutter incorporating a laser producing a beam of light for cutting the segment of skin along the lifted portion; and a controller adapted to control said skin lifting element and said laser, whereby the segment of skin is successively lifted and cut and removed from said body for use as a graft.

2. The skin graft harvesting apparatus of claim 1, further comprising:

a laser beam directing assembly mounted to said support frame for directing the beam produced by said laser along the portion of skin being harvested.

3. The skin graft harvesting apparatus of claim 2, wherein said directing assembly includes:

a stage;

a motor for driving said stage; and wherein said controller is adapted to control said motor so that the beam of light produced by said laser cuts the segment of skin to a controlled size and thickness corresponding to a desired size and thickness for the graft.

4. An apparatus for harvesting a segment of skin from a body for later use as a graft comprising;

a support frame;

a skin lifting element mounted to said support frame for lifting a portion of skin; and a laser producing a beam of light for cutting the segment of skin along the lifted portion wherein said skin lifting element includes;

a roller; and adhesive tape attached to said roller for adhering to the portion of skin being lifted, whereby upon movement of said roller the portion of skin is progressively lifted and cut by the laser beam and the cut portion of skin is held against said roller.

5. An apparatus for harvesting a segment of skin from a body for later use as a graft, comprising;

a support frame;

a skin lifting element mounted to said support frame for lifting a portion of skin; and a laser producing a beam of light for cutting the segment of skin along the lifted portion wherein said skin lifting element includes:

a vacuum generating means;

a roller attached to said vacuum generating means, said roller including a plurality of holes to allow application of a vacuum force sufficient to lift and hold the portion of skin against said roller, whereby upon movement of said roller, the portion of skin is progressively lifted and cut by the laser beam and the cut portion of skin is held against said roller.

6. An apparatus for harvesting a segment of skin from a body for later use as a graft comprising:

a support frame;

a roller mounted to said frame for lifting a portion of skin;

a laser producing a beam of light for cutting the segment of skin along the lifted portion, whereby the segment of skin is successively lifted and cut and removed for use as a graft.

7. The skin graft harvesting apparatus of claim 6, further comprising:

a stage mounted on said support frame; and a director attached to said stage for adjustably directing the beam of light toward the lifted portion of said segment of skin being harvested.

8. The skin graft harvesting apparatus of claim 7, further comprising:

a shaft mounted to said support frame, said shaft supporting linear and rotational movement of said stage about the axis of said shaft;

a first motor for driving said stage linearly along said shaft;

a second motor for driving said stage rotationally about said shaft; and a controller for said motors, whereby the movement of said stage along and about said shaft is controlled so that the laser beam cuts the portion of skin to a size and thickness corresponding to a desired size and thickness for the graft.

9. The skin graft harvesting apparatus of claim 8, further comprising:

a pulley system attached to said stage and to said first motor for driving said stage along said shaft; and a lever attached to said stage at one end and to said second motor at a second end for driving said stage rotationally about the axis of said shaft.

10. The skin graft harvesting apparatus of claim 8, further comprising:

adhesive tape attached to said roller for adhering to the portion of skin being lifted; and a third motor for driving said roller, said third motor controlled by said controller.

11. The skin graft harvesting apparatus of claim 8, further comprising:

a vacuum generating means attached to said roller; and wherein said roller includes a plurality of holes to allow application of a vacuum force sufficient to lift and hold the portion of skin against said roller, whereby upon movement of said roller the portion of skin is lifted for cutting by said laser and the cut segment of skin is held against said roller as the segment of skin is progressively severed by the laser beam.

12. A method of harvesting a segment of skin from a body to serve as a graft includes the steps of:

lifting a portion of skin;

cutting the portion of skin with a beam of light generated by a laser; and raising the cut portion of skin to allow further cutting by the laser beam, whereby the portions of skin are successively lifted, cut and raised until the desired size graft is severed from the body.

13. The method of harvesting a segment of skin of claim 12, wherein the step of lifting a portion of skin includes placing a roller having a skin attracting media applied thereto on the segment of skin;

and rotating said roller.

14. The method of harvesting a segment of skin of claim 13, wherein the step of cutting the portion of skin includes directing a laser beam toward the portion of skin; and driving the laser from a first side of the portion of skin to a second side dependent upon the desired size of graft, whereby as successive cuts are made by the laser beam the roller lifts the cut portion of skin for successive cutting and lifting operations until the desired size of graft is obtained.

15. A method of harvesting a segment of skin from a body to serve as a graft comprising the steps of:

placing a roller attached to a vacuum generating means and having a plurality of holes to allow application of a vacuum force sufficient to lift and hold a portion of skin against the roller in contact with the segment of skin to be harvested;

driving said roller a first distance to lift the portion of skin;

cutting the portion of skin with a laser beam of light generated by a laser; and removing the segment of skin severed by successive driving and cutting operations, whereby the laser beam cuts the segment of skin to a predetermined size and thickness corresponding to a desired size and thickness for the graft.

* * * * *